United States Patent [19]

Kawamatsu et al.

[11] 4,387,101

[45] Jun. 7, 1983

[54] THIAZOLIDINE DERIVATIVES AND THEIR USE

[75] Inventors: Yutaka Kawamatsu, Kyoto; Yujiro Yamamoto, Suita, both of Japan

[73] Assignees: Takeda Chemical Industries, Ltd.; Senju Pharmaceutical Co., Ltd., both of Osaka, Japan

[21] Appl. No.: 227,786

[22] Filed: Jan. 21, 1981

[30] Foreign Application Priority Data

Jan. 24, 1980 [JP] Japan .................................. 55-7558
Jul. 29, 1980 [JP] Japan ................................ 55-104718

[51] Int. Cl.³ ................. C07D 277/04; A61K 31/425
[52] U.S. Cl. .................................... 424/270; 548/183
[58] Field of Search ......................... 548/183; 424/270

[56] References Cited

U.S. PATENT DOCUMENTS

| 2,678,318 | 10/1952 | Heilbron et al. | 548/183 |
| 3,311,655 | 3/1967 | Boileau et al. | 548/183 |
| 3,825,553 | 7/1974 | Diamond et al. | 260/306.7 |
| 4,186,129 | 1/1980 | Huth et al. | 424/270 |
| 4,340,605 | 7/1982 | Kawamatsu et al. | 548/183 |
| 4,349,683 | 9/1982 | Bigg | 548/183 |

FOREIGN PATENT DOCUMENTS 8203 2/1980 European Pat. Off. .

OTHER PUBLICATIONS

Burton et al., Jour. of Medicinal Chemistry, vol. 13, pp. 1009-1012, (1970).

Primary Examiner—Nicholas S. Rizzo
Attorney, Agent, or Firm—Wenderoth, Lind & Ponack

[57] ABSTRACT

A thiazolidine derivatives of the formula:

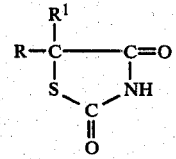

wherein R is a phenyl group having 2 nuclear substituent groups selected from the group consisting of a lower alkyl having 1 to 6 carbon atoms, a lower alkoxy having 1 to 7 carbon atoms, hydroxyl and a carboxylic acyloxy having 1 to 4 carbon atoms, or a phenyl group having a methylenedioxy group in adjacent positions on its ring; $R^1$ is H or an alkyl having 1 to 6 carbon atoms, or a physiologically acceptable salt thereof is a novel compound having the activity to control certain chronic symptoms due to diabetes, such as diabetic cataract, diabetic neuropathy and diabetic retinosis.

7 Claims, No Drawings

THIAZOLIDINE DERIVATIVES AND THEIR USE

This invention relates to a novel thiazolidine derivative having the activity to control certain chronic symptoms due to diabetes, such as diabetic cataract and diabetic neuropathy, its production and its use as a therapeutic agent for diabetic cataract, diabetic neuropathy and diabetic retinosis.

More particularly, this invention relates to:

1. A thiazolidine derivative of the general formula:

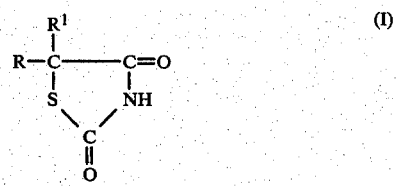

wherein R is a phenyl group having 2 nuclear substituent groups selected from the group consisting of an alkyl having 1 to 6 carbon atoms, an alkoxy having 1 to 7 carbon atoms, hydroxyl and a carboxylic acyloxy having 1 to 4 carbon atoms, or a phenyl group having a methylenedioxy group in adjacent positions on its ring; $R^1$ is hydrogen or an alkyl having 1 to 6 carbon atoms, or a physiologically acceptable salt thereof.

2. A method of producing a thiazolidine derivative of the formula (I), which comprises hydrolyzing a compound of the formula:

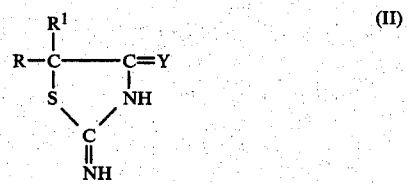

wherein R and $R^1$ have the meanings given above and Y is oxygen or imino.

3. A medicinal composition for the treatment of a mammal suffering from diabetic cataract, diabetic neuropathy or diabetic retinosis, which comprises, as an active ingredient, an effective amount of a compound of the formula (I) or a physiologically acceptable salt thereof, and a physiologically acceptable carrier, excipient or diluent therefor.

Referring to the formulas (I) and (II), the alkyl having 1 to 6 carbon atoms as a substituent of R is a straight- or branched-chain alkyl such as methyl, ethyl, n-propyl, i-propyl, n-butyl, i-butyl, etc. and is preferably a lower alkyl having 1 to 4 carbon atoms. The alkoxy having 1 to 7 carbon atoms as a substituent of R includes methoxy, ethoxy, n-propoxy, i-propoxy, n-butoxy, i-butoxy, n-pentyloxy, i-pentyloxy, neopentyloxy, n-hexyloxy, i-hexyloxy, etc. The carboxylic acyloxy having 1 to 4 carbon atoms may for example be acetyloxy, propionyloxy, etc. The substituents may be located in optional positions on the phenyl group of R but are preferably present at 3- and 4-positions of the phenyl group. Particularly preferred compounds of this invention are those containing an alkoxy having 1 to 4 carbon atoms, especially ethoxy, in the 3-position mentioned just above. Where the 4-position is substituted by alkoxy, the alkoxy is preferably a group having 4 to 6 carbon atoms, such as n-butoxy, n-pentyloxy, etc. The alkyl having 1 to 6 carbon atoms designated by $R^1$ is a straight- or branched-chain alkyl such as methyl, ethyl, n-propyl, i-propyl, n-butyl, i-butyl, etc. As the physiologically acceptable salt of the compound (I), there may for example be metioned sodium salt, potassium salt, calcium salt, etc.

The thiazolidine derivative (I) has the ability to inhibit the activity of aldose reductase isolated from rat-lens or human-placenta and the ability to inhibit swelling im the rat-lens-culture-assay, and it is used for alleviation or therapy of diabetic cataract, diabetic neuropathy, diabetic retinosis, etc. in mammals (e.g. human being, mouse, rat, rabbit, dog and monkey).

The thiazolidine derivative (I) may be safely administered, orally, parenterally or locally as it is or advantageously as a pharmaceutical composition comprising an effective amount of the compound (I) and a physiologically acceptable carrier, excipient or diluent therefor, in the form of, for example, powder, granule, tablet, hard capsule, soft capsule, dry syrup, suppository, injection, pellet, ophthalmic solution or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carriers or excipients include lactose, starch, sugar, magnesium stearate, etc. As the excipients in the preparation of soft capsules, there may be used nontoxic, pharmaceutically acceptable oils and fats of animal, vegetable or mineral origin. The essential active ingredients are generally dissolved in these oils and fats before filling soft capsules therewith.

The compositions for local administration may, for example, be pellet and ophthalmic solution. The ophthalmic solution may be prepared in the form of solution or suspension by a known procedure.

The composition of this invention contains a drug of dosage unit form. The drug of dosage unit form means a drug containing a daily dose of the compound (I) to be described hereinafter, or its multiples (up to 4 times), or its measures (down to 1/40), which is in a physically separate unit form suitable for administering as a medicine.

The dosage of the compound (I) varies with the kinds of diseases, symptoms, administration routes or dosage forms, but in case of oral administration, the daily dose is about 0.2 mg to 1000 mg (0.004 mg to 20 mg/kg), preferably 30 to 300 mg (0.6 mg to 6 mg/kg) for adult humans. For ophthalmic use, a 0.001 to 1% ophthalmic solution is desirably administered to the eye at the frequency of 3 to 5 times daily, one to a few drops a time.

In a test in mice (each group consisting of 5 mice), when the compounds (I), for example, 5-(3-ethoxy-4-pentyloxyphenyl)thiazolidine-2,4-dione and 5-(3-ethoxy-4-isopentyloxyphenyl)thiazolidine-2,4-dione were administered at a dose of 2500 mg/kg once, no mouse died.

The thiazolidine derivative (I) of the present invention can be produced, for example, by hydrolyzing a compound of formula (II).

The compound (II) may exist in the following tautomeric forms but these compounds are represented by the formula (II) for simplicity.

When Y is oxygen

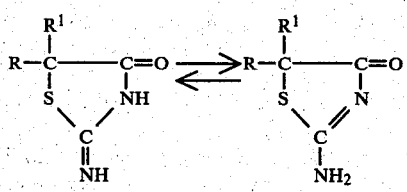

When Y is an imino group

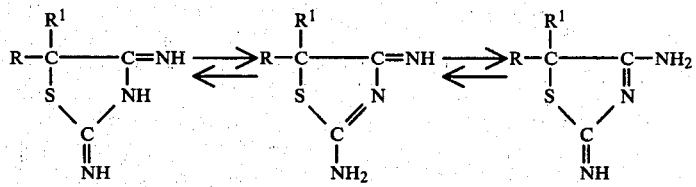

The hydrolysis reaction is compound (II) is carried out at an elevated temperature in a suitable solvent (e.g. sulfolane) and in the presence of water and mineral acid (e.g. sulfuric acid, hydrochloric acid, nitric acid, etc.). The amount of acid is usually 0.1 to 10 moles and preferably 0.2 to 3 moles to each mole of compound (II). The amount of water is usually a large excess over compound (II). The heating time is usually a few hours to several more than 10 hours.

The compound (I) wherein $R^1$ is a lower alkyl having 1 to 6 carbon atoms, can also be prepared by treating a compound of the formula:

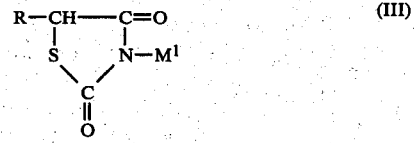 (III)

[wherein R is as defined hereinbefore; $M^1$ is an alkali metal atom such as sodium or potassium] with a strong base to give a dianion and, then, reacting the dianion with an alkylating agent such as an alkyl halide. The strong base may commonly be a lithium-diisopropylamide system. This alkylation reaction is usually conducted in a solvent. Examples of the solvent include ethyl ether, tetrahydrofuran, dioxane, dimethoxyethane and other ethers. The proportions of the strong base and alkylating agent are equimolar with respect to compound (III). The temperature and other conditions of this reaction depend on the starting materials, solvent, etc. but usually the reaction is conducted at 0° C. to 50° C. for an hour to several more than 10 hours.

The thiazolidine derivative (I) thus produced can be isolated and purified by conventional separation-purification methods, such as concentration, concentration under reduced pressure, solvent extraction, crystallization, recrystallization, phasic transfer or redistribution, and chromatography.

The compound (II) can be prepared by reacting a compound of the formula:

 (IV)

wherein R and $R^1$ are as defined above; X is a halogen; Z is nitrile, carboxyl, alkoxycarbonyl, aminocarbonyl or a group of the formula: $COOM^2$ (wherein $M^2$ is an alkali metal or ammonium) with thiourea. This reaction is usually carried out in a solvent. The solvent includes, for example, alcohols (e.g. methanol, ethanol, propanol, butanol, ethylene glycol monomethyl ether), ethers (e.g. tetrahydrofuran, dioxane), acetone, dimethylsulfoxide, sulfolane and dimethylformamide. The ratio of the reactants is not critical but it is usually recommended to employ equimolar amounts or a slight excess of thiourea to each mole of compound (IV). A preferred ratio is 1 to 2 moles per mole of (IV). The reaction conditions such as temperature and time depend on the starting compound, solvent and other factors but usually the reaction is conducted at the boiling temperature of the solvent or at a temperature between 100° C. and 130° C. for more than 10 minutes, preferably 30 minutes to several more than 10 hours. The reaction gives a compound (II) which is sparingly soluble. This step is followed by a hydrolysis procedure, with or without a step of isolating compound (II).

The compound (II) can also be prepared by reacting a compound of the formula:

 (V)

wherein R and $R^1$ are as defined above, with thiourea in the presence of an acid. This reaction is usually carried out in a solvent. The solvent includes, for example, alcohols (e.g. methanol, ethanol, propanol, butanol, ethylene glycol monomethyl ether), ethers (e.g. tetrahydrofuran, dioxane), dimethylsulfoxide, sulfolane and dimethylformamide. As an acid, there may be mentioned acetic acid, hydrochloric acid, phosphoric acid, sulfuric acid etc. The acid is usually employed in an amount of 0.5 to 3 equivalents relative to compound (V). The ratio of the reactants is not critical but it is usually recommended to employ equimolar amounts or a slight excess of thiourea to each mole of compound (V). A preferred ratio is 1 to 2 moles per mole of (V). The reaction conditions such as temperature and time depend on the starting compound, solvent and other factors but usually the reaction is conducted at 50° C.-60° C. for more than 20 minutes, preferably 30 minutes to several more than 10 hour. The reaction also gives a compound (II). This step is followed by a hydrolysis procedure, with or without a step of isolating compound (II). In the reaction of this step, the compound (V) reacts with thiourea in the presence of an acid to give the compound (II), while 2,4-diiminothiazolidine compound, heretofore, has been prepared by firstly reacting cyanohydrin compound with thionyl chloride to give an α-chloroacetonitrile compound, and then, reacting the α-chloroacetonitrile compound with thiourea. According to the reaction of this step, the yield of the compound (II) is higher than that in the method which gives compound (II) from compound (V) via an α-chloroacetonitrile compound.

The compounds (IV) and (V) can be prepared by the following route.

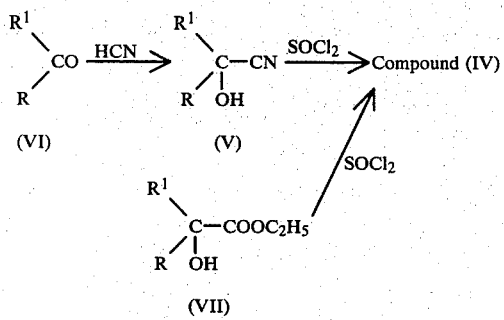

The following reference examples, working examples and experimental data are given to further illustrate this invention.

REFERENCE EXAMPLE 1

4.8 g of α-chloro-α-(3,4-diethoxyphenyl)acetonitrile and 2.3 g of thiourea, in 70 ml of ethanol, are stirred under reflux for 1 hour. After cooling, the solution is poured in 200 ml of water, neutralized with a saturated aqueous solution of sodium hydrogen carbonate and extracted with chloroform. The extract is washed with water, dried (MgSO$_4$) and distilled to remove the chloroform. The above procedure provides 3.9 g (69.6%) of 5-(3,4-diethoxyphenyl)-2,4-diiminothiazolidine, m.p. 185°–190° C.

REFERENCE EXAMPLE 2

730 mg of ethyl α-chloro-α-(2,4-diethoxyphenyl)acetate and 380 mg of thiourea, in 7 ml of ethanol, are stirred under reflux for 1 hour. After cooling, the solution is poured in 30 ml of water, neutralized with a saturated aqueous solution of sodium hydrogen carbonate and extracted with ethyl acetate. The extract is washed with water, dried (MgSO$_4$) and distilled to remove the ethyl acetate, whereby 510 mg (74.5%) of 5-(2,4-diethoxyphenyl)-2-iminothiazolidin-4-one is obtained, m.p. 179°–181° C. (hemihydrate).

REFERENCE EXAMPLE 3

(a) In 200 ml of ethyl acetate is dissolved 25 g of 3,4-diethoxybenzaldehyde and under cooling in an ice-NaCl bath, a solution of 67 g of sodium hydrogen sulfite in 100 ml of water and a solution of 42 g of potassium cyanide in 60 ml of water are added dropwise in that order. The mixture is kept stirred under ice-cooling for 7 hours. The organic layer is then separated, washed with water, dried (MgSO$_4$) and distilled under reduced pressure to remove the solvent. The above procedure provides 23.0 g (81.3%) of crystals of α-(3,4-diethoxyphenyl)-α-hydroxyacetonitrile. Recrystallization from ether-n-hexane gives colorless platelets, m.p. 71°–72° C.

(b) In 60 ml of chloroform is dissolved 4.4 g of α-(3,4-diethoxyphenyl)-α-hydroxyacetonitrile and after addition of 1.5 ml of thionyl chloride, the mixture is heated under reflux for 15 minutes. After cooling, the reaction mixture is washed with a saturated aqueous solution of sodium hydrogen carbonate and water in the order mentioned, followed by drying over MgSO$_4$. The solvent is then distilled off to give 4.8 g of a crude oil of α-chloro-α-(3,4-diethoxyphenyl)acetonitrile (quantitative yield). [If desired, this crude oil as it is can be used in the next reaction step.] The above crude oil is then purified by column chromatography (eluent: ether-n-hexane=1:5) and the resulting crystals are recrystallized from n-hexane. Colorless needles, m.p. 61°–62° C.

REFERENCE EXAMPLE 4

In 45 ml of methanol is dissolved 11.8 g of 3-ethoxy-4-pentyloxybenzaldehyde. While the solution is stirred at a temperature not exceeding 15° C., 4.1 ml of concentrated hydrochloric acid and 7 ml of aqueous solution of sodium cyanide (2.81 g) are added in that order. The mixture is stirred at room temperature for 0.5 hours and poured into 300 ml of cold water. To the reaction mixture is added 300 ml of hexane-ether (2:1) and the mixture is shaken well. The upper layer is separated, washed with 100 ml of water three times and dried (MgSO$_4$). The solvent is distilled off under reduced pressure, whereby 12.9 g of pale yellow oil is obtained. The above oil is then purified by column chromatography (eluent: chloroform) to give pale yellow oil of α-(3-ethoxy-4-pentyloxyphenyl)-6θ-hydroxyacetonitrile.

REFERENCE EXAMPLE 5

In 50 ml of methanol is dissolved 500 mg of 5-(3,4-diethoxyphenyl)thiazolidine-2,4-dione and after addition of 1 ml of a 2 N-methanolic solution of sodium methoxide, the solvent is distilled off under reduced pressure. The residual crystals are treated with ether and recovered by filtration to give 410 mg (76.1%) of 5-(3,4-diethoxyphenyl)thiazolidine-2,4-dione sodium salt. Recrystallization is carried out from ethanol-ether, m.p. 254°–255° C. (decomp.).

EXAMPLE 1

In a mixture of 40 ml ethanol and 40 ml 2 N-HCl is dissolved 2.8 g of 5-(3,4-diethoxyphenyl)-2,4-diiminothiazolidine and the solution is heated under reflux for 8 hours. After cooling, water is added and extraction is carried out with chloroform. The extract is washed with water, dried (MgSO$_4$) and distilled to remove the chloroform. The above procedure provides 2.6 g (92.9%) of crystals of 5-(3,4-diethoxyphenyl)thiazolidine-2,4-dione. Recrystallization from methanol gives colorless prisms, m.p. 139°–140° C.

EXAMPLE 2

In a mixture of 5 ml of ethanol and 4 ml of 2 N-HCl is dissolved 500 mg of 5-(2,4-diethoxyphenyl)-2-iminothiazolidin-4-one and the solution is heated under reflux for 8 hours. After cooling, water is added and extraction is carried out with chloroform. The extract is washed with water, dried (MgSO$_4$) and distilled to remove the chloroform. The above procedure provides 420 mg (84%) of crystals of 5-(2,4-diethoxyphenyl)thiazolidine-2,4-dione. Recrystallization from ether-n-hexane gives colorless prisms, m.p. 137°–138° C.

EXAMPLE 3

1.0 g of α-chloro-α-(3,4-diethoxyphenyl)acetonitrile and 477 mg of thiourea, in 20 ml of ethanol, are stirred under reflux for 10 hours. Then, 20 ml of 2 N-HCl is added and the mixture is heated under reflux for another 10 hours. After cooling, water is added and extraction is carried out with chloroform. The extract is washed with water, dried (MgSO$_4$) and distilled to remove the chloroform. The precedure provides 870 mg (73.7%) of crystals of 5-(3,4-diethoxyphenyl)-thiazolidine-2,4-dione.

EXAMPLE 4

24.6 g of α-chloro-α-(3-ethoxy-4-pentyloxyphenyl)acetonitrile and 10.2 g of thiourea in 100 ml of ethylene glycol monomethyl ether are stirred at 90°–100° C. for 10 minutes. After addition of 150 ml of 2 N-HCl at 110° C., the mixture is further stirred for 15 hours. After cooling, water is added and extraction is carried out with ethyl acetate. The extract is washed with water, dried (MgSO$_4$) and distilled to remove the solvent. The above procedure gives 16 g (56.2%) of 5-(3-ethoxy-4-pentyloxyphenyl)-thiazolidine-2,4-dione. Recrystallization from dilute ethanol gives colorless platelets, m.p. 104.5°–106° C.

EXAMPLE 5

2.26 g of ethyl α-chloro-α-(3,4-dimethylphenyl)acetate and 910 mg of thiourea, in 15 ml of ethylene glycol monoethyl ether, are stirred under reflux for 2 hours. Then, 1 ml of concentrated HCl is added and the mixture is further heated under reflux for 3.5 hours. After cooling, water is added and extraction is carried out with ethyl acetate. The extract is washed with water and dried (MgSO$_4$). After the solvent is distilled off, column chromatography is carried out on the oily residue with 100 g of silica gel. The eluate with chloroform-ethyl acetate (5:1) yields crystals of 5-(3,4-dimethylphenyl)thiazolidine-2,4-dione 1.32 g (60%). Recrystallization from cyclohexane-ethyl acetate gives colorless prisms, m.p. 121°–122° C.

EXAMPLE 6

In 4 ml of 2-methoxyethanol is dissolved 2 g of α-(3-ethoxy-4-pentyloxyphenyl)-α-hydroxyacetonitrile. To the solution, 866 mg of thiourea and 2.75 ml of concentrated hydrochloric acid are added. The mixture is stirred at 57° C.–65° C. for 2 hours. After adding 1 ml of water the mixture is refluxed for 5 hours. To the reaction mixture are added 15 ml of hexane-ethyl acetate (25:3) and 15 ml of water. The resulting crystals are collected by filtration, whereby 2.1 g of 5-(3-ethoxy-4-pentyloxyphenyl)thiazolidine-2,4-dione is obtained as scale-like colorless crystals.

EXAMPLE 7

In 7.5 ml of 2-methoxyethanol is dissolved 2.36 g of 3-ethoxy-4-pentyloxybenzaldehyde. While the solution is stirred at a temperature not exceeding 25° C., 0.83 ml of concentrated hydrochloric acid and solution of 0.56 g sodium cyanide in 1.5 ml of water are added in that order. After the solution is stirred for one hour, 1.14 g of thiourea and 3.6 ml of concentrated hydrochloric acid are added to the solution. The solution is stirred at 60° C.–65° C. for 2.5 hours and refluxed for 4 hours. After cooling the reaction mixture, 22 ml of hexane-ethyl acetate (25:3) and 15 ml of water is added. The mixture is stirred for 0.5 hour to give crystals. The crystals are collected by filtration and dried. The procedure gives 2.2 g of 5-(3-ethoxy-4-pentyloxyphenyl)-thiazolidine-2,4-dione as scalelike colorless crystals. Recrystallization from diluted ethanol gives crystals melting at 104° C.–105° C.

EXAMPLE 8

In 50 ml of 2-methoxyethanol is dissolved 23.6 g of 3-ethoxy-4-pentyloxybenzaldehyde. While the solution is stirred at 20° C., 6.9 g of acetic acid and a solution of 5.64 g sodium cyanide in 10 ml of water are added in that order. After the solution is stirred for 0.5 hour, 11.4 g of thiourea and 36 ml of concentrated hydrochloric acid are added to the solution. The solution is stirred at 57° C.–64° C. for 2 hours and refluxed for 4 hours. After cooling the reaction mixture, 224 ml of hexane-ethyl acetate (25:3) and 150 ml of water are added. The mixture is stirred on a ice-bath for 0.5 hour. The resulting crystals are collected by filtration and dried. The procedure gives 25.0 g of 5-(3-ethoxy-4-pentyloxyphenyl)-thiazolidine-2,4-dione as scale-like colorless crystals. Recrystallization from diluted ethanol gives crystals melting at 104° C.–105° C.

EXAMPLE 9

In 200 ml of anhydrous tetrahydrofuran is dissolved 1.0 g of diisopropylamine, followed by the addition of 440 mg of 60% oily sodium hydride and 2.8 g of 5-(3,4-diethoxyphenyl)thiazolidine-2,4-dione in that order. The mixture is stirred at 50° C. for 30 minutes. The solution is cooled to 0° C. and 6.2 ml of a standard solution of n-butyllithium in hexane (1.62 N) is added dropwise at a temperature not exceeding 5° C. The mixture is further stirred at 30° C. for 15 minutes, after which time it is cooled again to 0° C. and a solution of 1.6 g ethyl iodide in 10 ml tetrahydrofuran is added dropwise. The mixture is stirred at 35° C. for 1 hour and then, 50 ml of water and 20 ml of 2 N-HCl are added dropwise in the order mentioned at a temperature not exceeding 15° C., followed by extraction with ethyl acetate. The extract is washed with water, dried (MgSO$_4$) and distilled to remove the solvent. Column chromatography is carried out on the oily residue with 50 g of silica gel. The fraction obtained with cyclohexane-ethyl acetate (4:1) provides 1.65 g (58.2%) of crystals of 5-(3,4-diethoxyphenyl)-5-ethylthiazolidine-2,4-dione. Recrystallization from ether-n-hexane gives colorless prisms, m.p. 79° C.–80° C.

EXAMPLE 10

Compounds No. 1 to 20 are synthesized by the same procedure as that described below.

TABLE 1

$$\underset{\underset{CO}{S}}{R-CH}-\underset{NH}{CO}$$

| No. | R | m.p. (°C.) | Recrystallization solvent | Corresponding Example No.* | Yield % |
|---|---|---|---|---|---|
| 1 | 3,4-(CH$_3$O)$_2$C$_6$H$_3$– | 177–178 | Methanol | Ref. 1 + Ex 1<br>Ex 3<br>Ex 6<br>Ex 7 | 21<br>25<br>85<br>75 |
| 2 | 3,4-(C$_2$H$_5$O)$_2$C$_6$H$_3$– | 139–140 | Methanol | Ex 6<br>Ex 7 | 88<br>77 |
| 3 | 3-C$_2$H$_5$O-4-HO-C$_6$H$_3$– | 195–196 | Ethanol-ethyl acetate | Ex 3<br>Ex 6<br>Ex 7 | 49<br>76<br>70 |
| 4 | 3-C$_2$H$_5$O-4-CH$_3$CO.O-C$_6$H$_3$– | 120–121 | n-hexane-ethyl acetate | Ex 3 | 10 |
| 5 | 3,4-(CH$_3$CO.O)$_2$C$_6$H$_3$– | 134–135 | n-hexane ethyl acetate | Ex 3 | 10 |
| 6 | 3,4-(HO)$_2$C$_6$H$_3$– | 186–187 (decomp.) | n-hexane ethyl acetate | Ex 3<br>Ex 6<br>Ex 7 | 51<br>75<br>60 |
| 7 | 3,4-methylenedioxy-C$_6$H$_3$– | 177–178 | Ethanol-water | Ex 3<br>Ex 6<br>Ex 7 | 55<br>72<br>65 |
| 8 | 3,4-(C$_4$H$_9$O)$_2$C$_6$H$_3$– | 113–115 | Cyclohexane-ethyl acetate | Ex 3<br>Ex 6<br>Ex 7 | 61<br>82<br>73 |
| 9 | 3-C$_2$H$_5$O-4-C$_4$H$_9$O-C$_6$H$_3$– | 111–112 | n-hexane-ethyl acetate | Ex 3<br>Ex 6<br>Ex 7 | 60<br>83<br>78 |
| 10 | 3,4-(C$_3$H$_7$O)$_2$C$_6$H$_3$– | 111–112 | Diluted ethanol | Ref. 1 + Ex 1<br>Ex 3<br>Ex 6<br>Ex 7 | 35<br>40<br>86<br>77 |
| 11 | 3,5-(C$_2$H$_5$O)$_2$C$_6$H$_3$– | 137–138 | Ether-n-hexane | Ex 6<br>Ex 7 | 78<br>70 |
| 12 | 3-C$_2$H$_5$O-4-C$_6$H$_{13}$O-C$_6$H$_3$– | 93–95 | Diluted ethanol | Ex 4<br>Ex 6<br>Ex 7 | 47<br>86<br>78 |
| 13 | 3-C$_2$H$_5$O-4-(i-C$_5$H$_{11}$O)-C$_6$H$_3$– | 127–128 | Methanol | Ex 4<br>Ex 6<br>Ex 7 | 53<br>85<br>74 |
| 14 | 3-C$_2$H$_5$O-4-(neo-C$_5$H$_{11}$O)-C$_6$H$_3$– | 115–116 | Diluted ethanol | Ex 4<br>Ex 6<br>Ex 7 | 46<br>78<br>72 |
| 15 | 3-C$_2$H$_5$O-4-(i-C$_6$H$_{13}$O)-C$_6$H$_3$– | 114–115 | 70% Ethanol | Ex 6<br>Ex 7 | 84<br>75 |

TABLE 1-continued $$\begin{array}{c} R-CH\text{------}CO \\ | \quad\quad\quad | \\ S \quad\quad\quad NH \\ \diagdown \quad\diagup \\ CO \end{array}$$

| No. | R | m.p. (°C.) | Recrystallization solvent | Corresponding Example No.* | Yield % |
|---|---|---|---|---|---|
| 16 | CH$_3$O—C$_6$H$_3$—, C$_4$H$_9$O— | 150–151 | n-Hexane-ethyl acetate | Ex 6<br>Ex 7 | 82<br>75 |
| 17 | CH$_3$O—C$_6$H$_3$—, C$_5$H$_{11}$O— | 143–144 | Ethanol | Ex 6<br>Ex 7 | 85<br>73 |
| 18 | CH$_3$O—C$_6$H$_3$—, C$_6$H$_{13}$O— | 133–134 | Ethanol | Ex 6<br>Ex 7 | 84<br>77 |
| 19 | CH$_3$O—C$_6$H$_3$—, iC$_6$H$_{13}$O— | 137–138 | 70% Ethanol | Ex 6<br>Ex 7 | 80<br>73 |
| 20 | C$_5$H$_{11}$O—C$_6$H$_3$—, CH$_3$O— | 109–110 | n-Hexane-ethyl acetate | Ex 6<br>Ex 7 | 82<br>76 |

*"Ref." means "Reference example" and "Ex." means "Example".

EXPERIMENT 1

The effect of the thiazolidine derivative (I) on aldose reductase activity was assayed after the method described in S. Haymen et al., Journal of Biological Chemistry, Vol. 240, 877 (1965) and Jin H. Kinoshita et al., Metabolism, Vol. 28, Nr. 4, Suppl 1, 462 (1979), etc. The enzyme used in the assay was a partially purified aldose reductase preparation from human placenta. The results for the respective compounds were expressed as % inhibition at the concentration of $10^{-6}$ mole and are shown in Table 2.

TABLE 2

| Compounds described in Examples | % Inhibition $10^{-6}$ M | Compounds described in Examples | % Inhibition $10^{-6}$ M |
|---|---|---|---|
| 10 - No. 1 | 57.1 | 10 - No. 2 | 57.0 |
| 10 - No. 3 | 51.6 | 10 - No. 4 | 59.0 |
| 10 - No. 5 | 76.9 | 10 - No. 6 | 41.8 |
| 10 - No. 7 | 47.4 | 5 | 35.8 |
| 10 - No. 8 | 51.7 | 10 - No. 9 | 55.2 |
| 10 - No. 10 | 53.5 | 4 | 34.6 |
| 10 - No. 12 | 37.7 | 10 - No. 13 | 34.0 |
| 10 - No. 14 | 28.0 | 10 - No. 15 | 60.6 |
| 10 - No. 16 | 38.7 | 10 - No. 17 | 40.6 |
| 10 - No. 18 | 32.2 | 10 - No. 19 | 68.1 |
| 10 - No. 20 | 30.0 | | |

EXPERIMENT 2

The swelling inhibitory effect of each compound in a rat lens culture assay was evaluated by the method described in H. Obazawa et al., Invest. Ophthalmol Vol. 13, Nr. 3, 204 (1974).

The result for each compound was expressed as the % inhibition of swelling into the lens at the concentration of $10^{-6}$ mole and are shown in Table 3.

TABLE 3

| Compounds described in Examples | % Inhibition $10^{-6}$ M |
|---|---|
| 10 - No. 1 | 30.3 |
| 10 - No. 2 | 37.0 |
| 10 - No. 4 | 23.7 |
| 4 | 44.6 |
| 10 - No. 12 | 33.0 |
| 10 - No. 13 | 25.3 |
| 10 - No. 14 | 57.2 |

EXAMPLE 11

An exemplary eye-drop formulation for the compound of this invention is as follows.

| (Eye drop) | |
|---|---|
| •Polyvinyl alcohol 500 | 500 mg |
| •Disodium phosphate.2H$_2$O | 200 mg |
| •Monosodium phosphate.12H$_2$O | 500 mg |
| •Sodium chloride | 750 mg |
| •Disodium edetate | 20 mg |
| •5-(3-Ethoxy-4-pentyloxyphenyl)thiazolidine-2,4-dione | 10 mg |
| •Benzalkonium chloride | 7 mg |
| Purified water to make a total volume of 100 ml | |

A typical formulation for the compound of this invention as a therapeutic agent for diabetic cataract, diabetic neuropathy or diabetic retinosis.

| (Tablet) | |
|---|---|
| (1) 5-(3-Ethoxy-4-pentyloxyphenyl)thiazolidine-2,4-dione | 10 mg |
| (2) Lactose | 35 mg |
| (3) Corn starch | 170 mg |
| (4) Microcrystalline cellulose | 30 mg |
| (5) Magnesium stearate | 5 mg |

-continued (Tablet)

250 mg
(per tablet)

The components (1), (2), and (3) and ⅔ of the component (4) are admixed and granulated. To the granules are added the remaining ⅓ of (4) and (5), and the mixture is molded into a tablet. The tablet is coated with a suitable coating material.

(Capsules)

| | |
|---|---|
| 5-(3-Ethoxy-4-isopentyloxyphenyl)thiazolidine-2,4-dione | 10 mg |
| Microcrystalline cellulose | 30 mg |
| Lactose | 57 mg |
| Magnesium stearate | 3 mg |
| | 100 mg |

The above ingredients are mixed in a conventional manner and gelatin capsules are filled with the mixture to prepare capsules.

(Tablet)

| | |
|---|---|
| 5-(3-Ethoxy-4-pentyloxyphenyl)thiazolidine-2,4-dione | 30 mg |
| Lactose | 44 mg |
| Starch | 10.6 mg |
| Starch (for making paste) | 5 mg |
| Magnesium stearate | 0.4 mg |
| Carboxymethylcellulose calcium | 20 mg |
| | 100 mg |

The above ingredients are mixed and made into tablets in a conventional manner.

(Soft capsule)

| | |
|---|---|
| 5-(3-Ethoxy-4-pentyloxyphenyl)thiazolidine-2,4-dione | 30 mg |
| Corn oil | 110 mg |
| | 140 mg |

The above ingredients are mixed to make a solution and then soft capsules are filled with the solution in a conventional manner.

What is claimed is:

1. A thiazolidine compound of the formula:

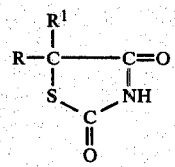

wherein R is phenyl having 2 nuclear substituents selected from the group consisting of alkyl having 1 to 6 carbon atoms, alkoxy having 1 to 7 carbon atoms, hydroxyl and carboxylic acyloxy having 1 to 4 carbon atoms, or R is phenyl having a methylenedioxy group in adjacent positions on its ring, and $R^1$ is hydrogen or alkyl having 1 to 6 carbon atoms, or a physiologically acceptable salt thereof.

2. A thiazolidine compound as claimed in claim 1, wherein $R^1$ is hydrogen.

3. A thiazolidine compound as claimed in claim 1, wherein R is a 3,4-dialkoxyphenyl group.

4. A thiazolidine compound as claimed in claim 1, wherein the thiazolidine derivative is 5-(3-ethoxy-4-pentyloxyphenyl)thiazolidine-2,4-dione.

5. A thiazolidine compound as claimed in claim 1, wherein the thiazolidine derivative is 5-(4-butoxy-3-ethoxyphenyl)thiazolidine-2,4-dione.

6. A medicinal composition for the treatment of a mammal suffering from diabetic cataract, diabetic neuropathy or diabetic retinosis, which comprises, (A) as an active ingredient, an effective amount of a compound of the formula:

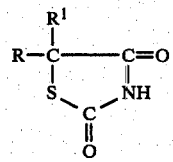

wherein R is phenyl having 2 nuclear substituents selected from the group consisting of alkyl having 1 to 6 carbon atoms, alkoxy having 1 to 7 carbon atoms, hydroxyl and carboxylic acyloxy having 1 to 4 carbon atoms, or R is phenyl having a methylenedioxy group in adjacent positions on its ring, and $R^1$ is hydrogen or alkyl having 1 to 6 carbon atoms, or a physiologically acceptable salt thereof, and (B) a physiologically acceptable carrier, excipient or diluent therefor.

7. A thiazolidine compound as claimed in claim 1, wherein the thiazolidine compound is 5-(3,4-dimethoxyphenyl)thiazolidine-2,4-dione.

* * * * *